(12) United States Patent
Kerrish et al.

(10) Patent No.: US 6,720,000 B2
(45) Date of Patent: Apr. 13, 2004

(54) PROCESS FOR PRODUCING WET RIBAVIRIN PELLETS

(75) Inventors: Donald J Kerrish, Wexford, PA (US); John R Bergeron, Baltimore, MD (US); Lawrence H Augsburger, Severna Park, MD (US)

(73) Assignee: Three Rivers Pharmaceutical, LLC, Pittsburgh, PA (US)

( * ) Notice: Subject to any disclaimer, the term of this patent is extended or adjusted under 35 U.S.C. 154(b) by 0 days.

(21) Appl. No.: 09/812,024

(22) Filed: Mar. 19, 2001

(65) Prior Publication Data

US 2003/0018000 A1 Jan. 23, 2003

(51) Int. Cl.$^7$ ................................................. A61K 9/48
(52) U.S. Cl. ........................................ 424/451; 514/43
(58) Field of Search ............................ 514/43; 424/451

(56) References Cited

U.S. PATENT DOCUMENTS

| | | | |
|---|---|---|---|
| 3,277,520 A | | 10/1966 | Nakahara ........................ 38/32 |
| 3,798,209 A | * | 3/1974 | Witkowski et al. ......... 536/28.7 |
| 3,927,216 A | | 12/1975 | Witkowski et al. ......... 424/269 |
| 3,948,885 A | * | 4/1976 | Witkowski et al. ......... 536/28.7 |
| 3,976,545 A | * | 8/1976 | Witkowski et al. ......... 536/28.7 |
| 4,138,547 A | * | 2/1979 | Christensen et al. ....... 536/28.7 |
| 4,211,771 A | | 7/1980 | Witkowski et al. ......... 424/180 |
| 5,405,837 A | | 4/1995 | Weber .......................... 514/23 |
| 5,767,097 A | | 6/1998 | Tam |
| 5,914,128 A | | 6/1999 | Liebowitz et al. |
| 5,916,594 A | | 6/1999 | Liebowitz et al. |
| 6,051,252 A | | 4/2000 | Liebowitz et al. |
| 6,063,772 A | | 5/2000 | Tam |
| 6,130,326 A | * | 10/2000 | Ramasamy et al. ........ 536/28.7 |
| 6,150,337 A | | 11/2000 | Tam |
| 6,172,046 B1 | | 1/2001 | Albrecht |
| 6,177,074 B1 | | 1/2001 | Glue et al. |
| 6,180,639 B1 | | 1/2001 | Coates et al. |
| 6,335,032 B1 | * | 1/2002 | Liebowitz et al. .......... 424/451 |
| 6,337,090 B1 | * | 1/2002 | Liebowitz et al. .......... 424/451 |
| 6,461,605 B1 | | 10/2002 | Cutler et al. |
| 6,472,373 B1 | | 10/2002 | Albrecht |
| 6,524,570 B1 | | 2/2003 | Glue et al. |
| 6,541,014 B2 | * | 4/2003 | Rudnic et al. ............... 424/400 |
| 2003/0104050 A1 | | 6/2003 | Matharu et al. |

FOREIGN PATENT DOCUMENTS

| | | |
|---|---|---|
| CA | 1261265 | 9/1989 |
| CA | 2135669 | 5/1996 |
| EP | 0 707 855 A2 | 4/1996 |
| WO | WO/9219227 | 11/1992 |
| WO | WO 96/36351 A1 | 11/1996 |
| WO | WO 03/039517 A1 | 5/2003 |

OTHER PUBLICATIONS

Eugene L. Parrott, Journal of Pharmaceutical Sciences, entitled,"Densification of Powders by Concavo–Convex Roller Compactor," vol. 70(3), 288–291 (Mar., 1981).

Ravin et al., "Preformulation," Chapter 75 in *Remington's Pharmaceutical Sciences, 18th Edition*, A. R. Gennaro et al. (eds.), 1990, Mack Publishing Co, Easton, PA, only pp. 1435–1450 supplied.*

Rudnic et al. (II), "Oral Solid Dosage Forms," Chapter 89 in *Remington's Pharmaceutical Sciences, 18th Edition*, A. R. Gennaro et al. (eds.), 1990, Mack Publishing Co, Easton, PA, only pp. 1633–1665 supplied.*

Porter, "Coating of Pharmaceutical Dosage Forms," Chapter 90 in *Remington's Pharmaceutical Sciences, 18th Edition*, A. R. Gennaro et al. (eds.), 1990, Mack Publishing Co, Easton, PA, only pp. 1666–1675 supplied.*

Longer et al., "Sustained–Release Drug Delivery Systems," Chapter 91 in *Remington's Pharmaceutical Sciences, 18th Edition*, A. R. Gennaro et al. (eds.), 1990, Mack Publishing Co, Easton, PA, only pp. 1676–1693 supplied.*

O'Connor et al. (I), "Powders," Chapter 88 in *Remington's Pharmaceutical Sciences, 18th Edition*, A. R. Gennaro et al. (eds.), 1990, Mack Publishing Co, Easton, PA, only pp. 1615–1632 supplied.*

O'Connor et al. (II), "Powders," Chapter 88 in Remington's Pharmaceutical Sciences, 18th Edition, A. R. Gennaro et al. (eds.), 1990, Mack Publishing Co, Easton, PA, only pp. 1598 and 1607 supplied.*

K. Marshall, "Compression and Consolidation of Powdered Solids," Chapter 4 in *The Theory and Practice of Industrial Pharmacy, Third Edition*, Lachman et al. (eds.), Lea & Febiger, Philadelphia, PA, 1986, only pp. 66–68 supplied.*

Botzolakis et al., "The role of disintegrants in hard–gelatin capsules", J. Pharm Pharmacol. (1984) 36, 77–84.

Eggleston, M "Clinical Review of Ribavirin", Clinical Pharmacology of Antibiotics, Infection Control (1987) vol. 3, No. 5, pp. 215–218.

Fernandez et al., "Ribavirin: A Clinical Overview", European Journal of Epidemiology (1986) vol. 2, No. 1, pp. 1–14 (03/96).

Hahn, F.E. "Mechnism of Action of Antieukaryotic and Antiviral Compounds", in: Hahn, F.E., *Antibiotics* (Springer–Verlag, New York, vol. V, Part 2, 1979) pp. 439–458.

(List continued on next page.)

*Primary Examiner*—James O. Wilson
*Assistant Examiner*—Lawrence E Crane
(74) *Attorney, Agent, or Firm*—McDermott, Will & Emery

(57) ABSTRACT

A process for producing wet ribavirin pellets is provided in order to make pharmaceutical dosages of ribavirin. The process is particularly useful as an alternative method for preparing pharmaceutical dosages of ribavirin that reduces the amount of ribavirin dust that is produced during the manufacturing process and allows for greater control of dissolution rates. According to the preferred embodiments, this method is accomplished through mixing ribavirin with at least one excipient into a uniform mixture, forming the mixture into a granulated mass by adding a wetting agent, shaping said granulated mass into soluble particles and drying the flowable particles. The process enables Ribavirin pharmaceutical pellets to be mixed with a binder and disintegrant to form a uniform mixture.

17 Claims, 1 Drawing Sheet

OTHER PUBLICATIONS

Merck Index—An Encyclopedia of Chemicals, Drugs, and Biologicals, Eleventh Edition, Budavari, ed. 1989, p. 1304.

Ormos, Z.D. "Ganulation and Coating" in: Chulia et al., ed. *Powder Technology and Pharmaceutical Processes* (New York, Elsevier, 1994) pp. 359–376.

Parikh, D. M. ed., *Handbook of Pharmaceutical Granulation Technology*, Chapters 1, 2, 11 (Marcel Dekker, New York, 1997) pp. 1–23 and 333–368.

Prusiner et al., "The Crystal and Molecular Structures of Two Polymorphic Crystalline Forms of Virazole (1—D—Ribofuranosyl–1,2,4–triazole–3–carboxamide). A New Synthetic Broad Spectrum Antiviral Agent", Acta Cryst. (1976). B32, 419, pp. 419–426.

Sidwell et al., "Broad–Spectrum Antiviral Activity of Virazole: 1—D–Ribofuranosyl–1,2,4–triazole–3–carboxamide", Science, (Aug. 25, 1972) vol. 177, No. 4050, pp. 705–706.

Sidwell et al., "Ribavirin: An Antiviral Agent", Pharmac. Ther. (1979) vol. 6, pp. 123–146.

*ICN Pharmaceuticals, Inc. v. Geneva Pharmaceuticals Technology Corp*, 2003 U.S. Dist. LEXIS 12024 (C.D. Cal. Jul. 14, 2003).

* cited by examiner

PROCESS FOR PRODUCING WET RIBAVIRIN PELLETS

BACKGROUND OF THE INVENTION

1. Field of the Invention

The present invention relates to a process for making oral pharmaceutical dosages of ribavirin. More specifically, the drug ribavirin is a synthetic nucleoside analog with broad spectrum antiviral activity. Ribavirin is one of a combination of drugs being administered to patients with Hepatitis C and other viral infections.

Ribavirin is currently manufactured, among other methods, using a process commonly called dry compaction. Dry compaction utilizes high pressure to form a ribbon of ribavirin that is subsequently reduced to a free flowing powder by milling. The undesirable side effects of manufacturing ribavirin by dry compaction include the creation of excessive dust, a potential health hazard, as well as the risk that high pressure, which can produce high heat, could produce polymorphic forms. Different polymorphs or combinations of polymorphs are undesirable because they can sometimes change the manner in which the active drug moiety is absorbed.

The present invention describes a method for manufacturing ribavirin using a wet granulation process. This process forms a free flowing ribavirin by mixing ribavirin with a wetting agent and various excipients to form a granulation that can be extruded and spheronized, producing a pellet. This process is not only an alternative method for producing ribavirin, but also offers several advantages over the dry compaction process. One advantage of wet granulation is that significantly less dust is produced, which is important from a health and safety standpoint. Another advantage of the present invention is that wet granulation allows for greater control of dissolution rates. In addition, this wet granulation method results in the ribavirin having better flow characteristics, enabling faster encapsulation and lower weight variations. Finally, because there is little heat or excessive pressure, the wet granulation method lowers the risk of creating polymorphs and, therefore, allows for greater uniformity of the crystalline structure.

2. Description of the Prior Art

It is well known in the art that a raw drug often is unsuitable for medicinal purposes because the raw drug has undesirable dissolution profiles and cannot be efficiently encapsulated because of poor flow qualities. For efficient encapsulation, proper flow is vital to producing a uniform, quality pharmaceutical product for a variety of reasons, including that these factors can affect how much active drug is absorbed and when it is absorbed into the human body.

Excipients are often added to raw drugs in order to create a mixture having improved flow, compaction, or disintegration characteristics. These excipients can add various qualities either to the end product or to some stage of the manufacturing process. Common excipients include disintegrants, lubricants, fillers, binders and wetting agents. Disintegrants absorb water quickly when the dosage form reaches the alimentary canal. Lubricants help with mold release and flow. Fillers provide bulk and, along with binders and wetting agents, add adhesion to the mixture. However, some formulas produce a finished dosage form that is too large or results in disintegration rates which could be slower or faster than is optimal.

The following three methods are commonly used to mix excipients with raw drugs to produce pharmaceutical capsules: (1) direct blend, (2) dry compaction, and (3) wet granulation. In the direct blend process, drugs and selected excipients are added to a blender and mixed in the dry state to produce a uniform distribution of the active drug. This direct blend method requires an active drug with acceptable flow characteristics. In the dry compaction process, drugs and selected excipients are mixed and then compacted into a ribbon and milled to a uniform particle size. This operation often generates heat. The result is a free flowing powder that can be encapsulated. Finally, in the wet granulation process, the drugs are mixed either in their liquid form or with a wetting agent to produce a wet mass that can be further processed to produce a free flowing material, which in turn can be encapsulated.

Heretofore, there have been no references in the prior art that demonstrate the successful use of the wet granulation process to manufacture ribavirin capsules. Rather ribavirin is presently made using a dry compaction process as shown in U.S. Pat. Nos. 6,051,252, 5,916,594 and 5,914,128. Each of U.S. Pat. Nos. 6,051,252, 5,916,594 and 5,914,128 describes a method of producing dosages of ribavirin using high pressures which could generate high temperatures. Specifically, U.S. Pat. Nos. 6,051,252 and 5,914,128 both describe the use of compressing forces that range from 50 to 75 kilonewtons of force.

Although the most common pharmaceutical dosage of ribavirin is 200 mg, other dosages could be manufactured.

SUMMARY OF THE INVENTION

It is, therefore, an object of the present invention to provide an alternative method for preparing pharmaceutical dosages of ribavirin which reduces the amount of ribavirin dust that is produced during the manufacturing process, allows for greater control of dissolution rates, and increases flow rates. This goal is accomplished through a wet granulation process that combines ribavirin with specific disintegrants, binders, fillers, and wetting agents in sufficient quantities to form an extrudable mass.

One preferred embodiment of the invention teaches that the extrudable mass is mixed to form a uniform mixture of active drug and excipients, which mixture is subsequently formed into pellets by extrusion and spheronization.

More specifically, the present invention is a process for producing ribavirin pellets, comprising the steps of mixing ribavirin with at least one excipient into a uniform mixture; forming said uniform mixture into a granulated mass by adding a wetting agent to said uniform mixture; shaping said granulated mass into flowable particles; and drying said flowable particles, resulting in dried flowable particles.

These objects, as well as other objects and advantages of the present invention, will become apparent from the following description, in reference to the illustrations and charts appended hereto.

BRIEF DESCRIPTION OF THE DRAWINGS

For a better understanding of the invention, refer to the accompanying chart in which.

Figure 1:
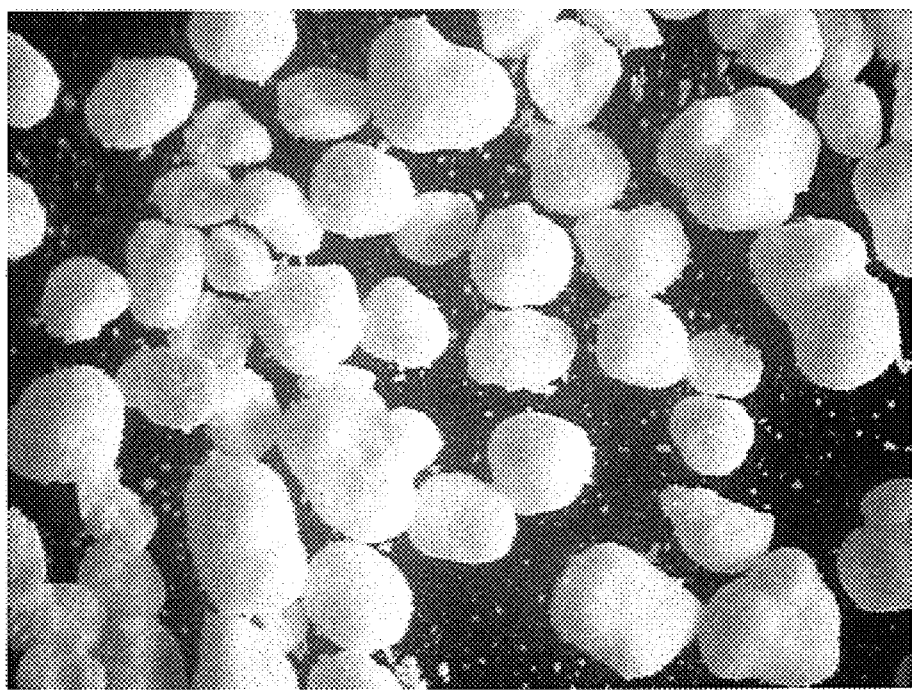
FIG. 1 is an electronic pho-

DETAILED DESCRIPTION OF THE PREFERRED EMBODIMENTS tograph of pellets produced by the preferred embodiment enlarged at a ratio of 1:1000.

The present invention discloses a process for making pharmaceutical dosages of ribavirin through wet granulation. There are several formulas that can be utilized to produce ribavirin pellets by wet granulation, preferably with extrusion and spheronization.

TABLE 1

| Formulation Ingredient | % Range of Total Formulation | Function in the Formulation |
|---|---|---|
| ribavirin | 31–35 | Active Pharmaceutical Ingredient |
| microcrystalline cellulose | 27–35.5 | Binder/Diluent |
| croscarmellose sodium | 0–3 | Disintegrant |
| polyethylene glycol | 11–39 | Binder/Wetting Agent |

Under one of the preferred embodiments, the dry ingredients listed in Table 1 above are mixed together and granulated with the wetting agent, extruded through a screen (0.4 millimeter ("mm") to 1.0 mm), spheronized, and fluid bed dried. Depending on the dosage required, the resulting pellets are filled into hard gelatin capsules sizes "1" to "00".

TABLE 2

| Formulation Ingredient | % Range of Total Formulation | Function in the Formulation |
|---|---|---|
| ribavirin, U.S. Pharmaceutical Grade ("USP") | 41–67 | Active Pharmaceutical Ingredient |
| microcrystalline cellulose | 24–33 | Binder/Diluent |
| croscarmellose sodium | 2–6 | Disintegrant |
| polyethylene glycol | 5–17 | Binder/Wetting Agent |
| povidone | 1–4.5 | Binder |
| water USP | 15–30 (calculated on a wet basis) | Wetting Agent |

Under another preferred embodiment, the dry ingredients listed in Table 2 above are mixed together and granulated with the wetting agent, extruded through a screen (0.4 mm to 1.0 mm), spheronized, and fluid bed dried. Depending on the dosage required, the resulting pellets are filled into hard gelatin capsules sizes "1" to "00".

TABLE 3

| Formulation Ingredient | % Range of Total Formulation | Function in the Formulation |
|---|---|---|
| ribavirin USP | 41–67 | Active Pharmaceutical Ingredient |
| microcrystalline cellulose | 24–33 | Binder/Diluent |
| croscarmellose sodium | 2–6 | Disintegrant |
| povidone | 1–4.5 | Binder |
| lactose | 5–10 | Diluent |
| water USP | 15–79 (calculated on a wet basis) | Wetting Agent |

Under another preferred embodiment, the dry ingredients listed in the Table 3 above are mixed together and granulated with the wetting agent, extruded through a screen (0.4 mm–1.0 mm), spheronized, and fluid bed dried. Depending on the dosage required, the resulting pellets are filled into hard gelatin capsules sizes "1" to "00".

One of the preferred embodiments results in a product that is encapsulated in size "1" or "1el" (elongated) capsules to form a 200 milligram ("mg") dose of active ribavirin. The total capsule weight is approximately 270 mg. One of the preferred embodiments also calls for a 200 mg pharmaceutical dosage in which at least 90% of the ribavirin dissolves within 30 minutes. Thus, although the method described in the claims can be used to produce ribavirin in different sized capsules or having different dissolution rates, this disclosure will only provide the detailed weights and other measurements that will result in a capsule containing 200 mg of active ribavirin having the previously mentioned rate of dissolution.

In the aforesaid preferred embodiment, the following formulation and material quantities are used most preferably:

TABLE 4

| Ingredient | % of Formulation | mg/ Capsule | kilogram ("kg")/ 10,000 Capsules 200 mg (size 1 el) | kg/ 10,000 Capsules 300 mg (size 0) | kg/ 1,000,000 Capsules 200 mg (size 1 el) | kg/ 1,000,000 Capsules 400 mg (size 00) |
|---|---|---|---|---|---|---|
| ribavirin USP | 74 | 200 | 2 | 3 | 200 | 400 |
| microcrystalline cellulose | 15.6 | 42 | 0.42 | 0.63 | 42 | 84 |
| croscarmellose sodium | 3.7 | 10 | 0.1 | 0.15 | 10 | 20 |
| povidone | 1.1 | 3 | 0.03 | 0.045 | 3 | 6 |
| lactose | 5.6 | 15 | 0.15 | 0.23 | 15 | 30 |
| water USP | | | 1.75 | 2.63 | 165 | 330 |
| Total | 100 | 270 | 2.7 | 4.05 | 270 | 540 |
| Total with Water USP | | | 4.45 | 6.68 | 435 | 870 |
| % Water USP in the wet granulation | | | 39 | 39 | 38 | 38 |

Ribavirin USP is mixed for 3 to 15 minutes along with microcrystalline cellulose, lactose monohydrate, croscarmellose sodium and povidone K 27–33 in a suitably sized granulator. Purified water USP is added to the mixture at a rate of 2 kg to 50 kg per minute. The wet mass is granulated for an additional 30 seconds to 20 minutes (depending on batch size).

After granulating, the wet mass is fed into an extruder at a rate that avoids product stagnation and excessive accumulation. The extruded mass is spheronized on an appropriately sized marumerizer or equivalent equipment using typical parameters. Typical parameters used during said spheronization include those listed as follows:

| | |
|---|---|
| Jacket water temperature | 45–60° C. |
| Groove plate configuration | Medium |
| Marumerizer speed setting | 0.5–1.0 |
| Spherionization time | 0.5–2 minute/portion |

In the aforesaid preferred embodiment, the pellets are fluid-bed dried.

Drying is continued until the pellets having a loss on drying (LOD) of not more than 5% and not less than 0.5% is achieved. Following drying, the pellets are sieved by use of a 16 mesh or 18 mesh screen.

After the pellets are sieved, said pellets can be used to fill a capsule employing standard encapsulators. In this preferred embodiment, the capsule is a size 1 elongated capsule which will have a desired total capsule fill weight of 270 mg.

Said preferred embodiment produces a dosage in which at least 90% will dissolve in 30 minutes. However, it is anticipated within this application that future uses of ribavirin may lead to a demand for ribavirin dosages having a different dissolution profile. Therefore, this invention discloses and claims the addition of coatings to the dried pellets to yield other dissolution profiles. Coatings in common use include polymethacrylic, dyethyl-aminophyl, polyethanene glycols and other excipients well known in the art.

We claim:

1. A process for producing ribavirin pellets, the process comprising:
    mixing ribavirin with at least one disintegrant, binder and filler to form a uniform mixture;
    adding water in the range of 15–79% of the total mixture as a wetting agent to wet said uniform mixture;
    extruding said wet uniform mixture through a screen;
    forming pellets of said extruded mixture;
    drying said pellets to form free flowing ribavirin pellets; and
    coating said dried pellets on an outside surface, resulting in a decreased rate of release of ribavirin during a given time span in comparison to the release under a condition without said coating.

2. A process for producing ribavirin pellets, the process comprising:
    forming a mixture comprising (i) from about 35% to about 80% of ribavirin by weight, (ii) at least a filler, and (iii) at least a disintegrant;
    adding water in the range of 15–79% of the total mixture as a wetting agent to said mixture to form an extrudable mass;
    extruding said mass;
    forming pellets of said extruded mass;
    drying said pellets to form free flowing ribavirin pellets; and
    coating said dried pellets on an outside surface, resulting in a decreased rate of release of ribavirin during a given time span in comparison to the release under a condition without said coating.

3. A process for producing ribavirin pellets, the process comprising:
    mixing ribavirin, microcrystalline cellulose, and croscarmellose sodium to form a mixture;
    adding water in the range of 15–79% of the total mixture to said mixture to form a wet granulate of said mixture;
    spheronizing said wet granulate to form uniform sized pellets;
    drying said pellets to form free flowing ribavirin pellets; and
    coating said dried pellets on an outside surface, resulting in a decreased rate of release of ribavirin during a given time span in comparison to the release under a condition without said coating.

4. The process of claim 1, further comprising filling a capsule with said coated pellets.

5. The process of claim 1, wherein said disintegrant, binder and filler are selected from the group consisting of povidone, starch, lactose, polyethylene glycol, hydroxy propyl methyl cellulose, croscarmellose sodium, microcrystalline cellulose, cellulose, sucrose and bentonite.

6. The process of claim 1, wherein the screen ranges in size from a 0.40 mm screen to a 1.0 mm screen.

7. The process of claim 1, wherein said step of drying comprises heating said pellets to a temperature ranging from about 35° C. to about 45° C., until said pellets contains a moisture content ranging from 0.5% to 5.0%.

8. The process of claim 2, further comprising filling a capsule with said coated pellets.

9. The process of claim 2, wherein said step of drying comprises heating said pellets to a temperature ranging from about 35° C. to about 45° C., until said pellets contains a moisture content ranging from 0.5% to 5.0%.

10. The process of claim 2, wherein said filler is selected from the group consisting of microcrystalline cellulose, lactose, sucrose, cellulose and starch.

11. The process of claim 2, wherein said disintegrant is selected from the group consisting of croscarmellose sodium, starch, cellulose and bentonite.

12. The process of claim 3, furhter comprising filling a capsule with said coated pellets.

13. The process of claim 3, wherein said step of drying comprises heating said pellets to a temperature ranging from about 35° C. to about 45° C., until said pellets contains a moisture content ranging from 0.5% to 5.0%.

14. A process of forming flowable ribavirin particles, the process comprising:
    mixing ribavirin with at least one disintegrant, binder and filler to form a uniform mixture;
    adding water in the range of 15–79% of the total mixture to wet said uniform mixture;
    shaping said wet mixture into particles; and
    drying said particles to form free flowing ribavirin containing particles.

15. The process of claim 14, wherein the water is added at a rate of about 2 kg per minute to about 50 kg per minute.

16. The process of claim 14, wherein said drying step comprises heating said particles to a temperature ranging from about 35° C. to about 45° C., until said particles contain a moisture content ranging from 0.5% to 5.0%.

17. The process of claim 14, wherein said shaping step is accomplished by spheronization.

* * * * *